United States Patent
Saito et al.

(10) Patent No.: US 6,839,134 B2
(45) Date of Patent: Jan. 4, 2005

(54) LIGHT MEASURING DEVICE AVOIDING INFLUENCE OF FLUORESCENCE OR PHOSPHORESCENCE OF LENSES AND FILTERS IN OPTICAL PATH

(75) Inventors: Michihiro Saito, Kashiwa (JP); Satoshi Takahashi, Hitachinaka (JP); Koichi Matsumoto, Hitachinaka (JP)

(73) Assignee: Hitachi, Ltd., Tokyo (JP)

( * ) Notice: Subject to any disclaimer, the term of this patent is extended or adjusted under 35 U.S.C. 154(b) by 0 days.

(21) Appl. No.: 10/255,623

(22) Filed: Sep. 27, 2002

(65) Prior Publication Data

US 2003/0133107 A1 Jul. 17, 2003

(30) Foreign Application Priority Data

Jan. 16, 2002 (JP) ........................................ 2002-006866

(51) Int. Cl.[7] .............................................. G01N 21/64
(52) U.S. Cl. ...................... 356/317; 250/458.1; 356/417
(58) Field of Search ................................ 356/317, 318, 356/417; 250/458.1, 459.1, 461.1, 461.2; 436/172; 422/82.08

(56) References Cited

U.S. PATENT DOCUMENTS 4,954,714 A 9/1990 Pollak et al. ............. 250/458.1

FOREIGN PATENT DOCUMENTS

| JP | 60-000420 | 1/1985 |
|---|---|---|
| JP | 04-106471 | 4/1992 |
| JP | 10-267844 | 10/1998 |
| JP | 2001-041889 | 2/2001 |

OTHER PUBLICATIONS

Verwoerd, N.P., et al., "Use of Ferro–Electric Liquid Crystal Shutters for Time–Resolved Fluorescence Microscopy", Wiley–Liss, Inc., vol. 16, Jun. 1994, pp. 113–117.

Vereb, Gyorgy, et al., "Temporally and Spectrally Resolved Imaging Microscopy of Lanthanide Chelates", Biophysical Journal, vol. 74, May 1998, pp. 2210–2222.

*Primary Examiner*—F. L. Evans
(74) *Attorney, Agent, or Firm*—Mattingly, Stanger & Malur, P.C.

(57) ABSTRACT

At the time of analytical measurement of a sample by the fluorescence measuring device or the phosphorescence measuring device, both the optical path of exciting light emitted from the light source to the sample and the optical path of fluorescence or phosphorescence emitted from the sample to the detection unit are shut off. Both are shut off by one chopper.

11 Claims, 6 Drawing Sheets

A : DECAY OF LIGHT BY EUROPIUM
B : DECAY OF NOISE LIGHT WHEN THE PRESENT INVENTION IS NOT USED
C : DECAY OF NOISE LIGHT WHEN THE PRESENT INVENTION IS USED

LIGHT SOURCE SIDE

LIGHT DETECTOR SIDE

LIGHT MEASURING DEVICE AVOIDING INFLUENCE OF FLUORESCENCE OR PHOSPHORESCENCE OF LENSES AND FILTERS IN OPTICAL PATH

BACKGROUND OF THE INVENTION

The present invention relates to a device for measuring fluorescence or phosphorescence emitted from a sample irradiated with excitation light, and more particularly to a fluorescence and phosphorescence measuring device capable of obtaining high detection sensitivity and SN ratio.

A fluorescence and phosphorescence measuring device detects a target component in an article to be measured using a phenomenon that when excitation light such as an excitation lamp or laser light is irradiated to a sample to be measured, the sample emits light with a wavelength different from the wavelength of the irradiated excitation light.

In an actual measuring device, at the time of measuring target emitted light from a sample, due to irradiation of exciting light to a sample container and an existing lens and filter, emitted light, fluorescence, or phosphorescence other than light from the target is measured and the measured SN ratio may be reduced.

Further, when light is measured on the confronting side of irradiating light, the afterglow of exciting light enters into a light measuring device and the SN ratio may be reduced in the same way. Namely, fluorescence or phosphorescence (hereinafter referred to as measurement interference light) not from a sample is analyzed and measured as if the article to be measured is included in the sample though the article to be measured is not naturally included in the sample and an incorrect judgment may be made.

Further, scattered light or measurement interference light is varied in intensity, as a result, the minimum detection limit of an applied analytical measuring method or a measuring device is remarkably reduced.

Conventionally, in order to reduce scattered light resulted from a lamp, a laser, an existing lens and filter, or a sample container, or interference light disturbing measurement, fluorescence is analyzed beforehand, and a raw material having smaller measurement interference light is selected and used as a material, and the use amount of material is reduced by making the material thinner, or the material surface is coated.

Further voltage, shape, and gas pressure were studied and the lamp and laser were improved so as to make an afterglow as little as possible after end of irradiation. With respect to the light measuring method, in addition to the transmission surface fluorescence measuring method that the exciting light irradiation direction coincides with the light measuring direction, the side fluorescence measuring method that the direction does not coincides and light from the lamp and laser is not directly taken in the detection unit and the irradiation surface fluorescence measuring method are properly used.

Furthermore, by development of a phosphor and a luminous body, the difference between the exciting light wavelength and the fluorescence or phosphorescence wavelength, the so-called stokes shift is increased, and a wavelength selection filter is installed, and avoidance of detection of light with a wavelength adjacent to the exciting light wavelength is executed.

Further, the time-resolved measuring method using a luminous body having a long fluorescence emission and phosphorescence emission continuous time and measuring fluorescence or phosphorescence during a time different from the exciting light irradiation time has been developed. In recent years, development of a luminous body particularly using a rare-earth element (Lantanoide) such as europium having a long stoke shift and a long light emission continuous time has been progressed and a method for labeling an article to be measured with it and executing analytical measurement has been improved.

However, in every method, scattered light or interference light disturbing measurement cannot be reduced sufficiently and an occurrence of interference light from articles other than a sample cannot be avoided.

In the time-resolved fluorescence measuring method, exciting light is said not to be taken in the light measuring device, and therefore, it is a normal way to set the fluorescence measuring time to the time that the exciting light is off. For example, it is a general method to turn on a flash lamp at 1000 Hz for 0.01 ms, measure between 0.4 ms and 0.8 ms after the lamp turns on, measure light in a 1-ms cycle, calculate the light quantity for 1 second, and display the data.

In a fluorescence measuring device or a phosphorescence measuring device, as a light source, a tungsten lamp, a mercury lamp, an argon gas lamp, a xenon flash lamp, a nitrogen gas laser, or an argon gas laser is used. As a method for preventing light other than the target light from irradiating a sample, a light shielding plate or an optical path shut-off plate (hereinafter referred to as a chopper) may be used.

On the circumference having a circular black plate, a gap with a fixed size is formed, and the black plate is rotated, and exciting light generated from the light source passes only through the gap, thus exciting light at a fixed time interval is irradiated to a sample.

In the light source, when the lamp is turned off, the light does not disappear instantaneously and the core of the light source reduces the light for a little while, thus even if the voltage is cut off, the light source generally emits light. The afterglow after the voltage is cut off lets the lens, filter, sample, or sample container of the light source or detection unit emit light sometimes, causing increasing of noise or background at the time of measurement.

Furthermore, the afterglow has a wavelength different from the original one of the light emitted from the light source, so that when exciting light is to be separated from fluorescence or phosphorescence in wavelength, the afterglow may have the same or close wavelength to that of fluorescence or phosphorescence, causing increasing of noise at the time of measurement. In order to remove the afterglow of the light source, it may be set so that the chopper ends breaking at the same time with or prior to turning off the power source of the light source.

In the time-resolved fluorescence measuring method, the exciting irradiation time to a sample and the measuring time of fluorescence or phosphorescence emitted from the sample are made different from each other, thus measurement of noise resulted from the exciting light is reduced and the sensitivity of measurement is increased.

In order to reduce the aforementioned noise or background, the chopper is put in front of the sample or the lens and filter of the light source and light other than the target is prevented from irradiation to the sample. Breaking by the chopper is synchronized with turning on or off the power source.

Furthermore, the lens, filter, or mirror receiving irradiation of light emitted from the light source may scatter the light. Scattered light is preferably prevented from irradiation to the sample. In order to prevent the afterglow of the lamp after the power is turned off from irradiation to the sample, the chopper is put on the optical path connecting the lamp and sample and light other than necessary light physically emitted from the light source is shielded.

By doing this, when the lamp is turned off, unnecessary light is prevented from irradiation to the sample and the sample emits fluorescence or phosphorescence, only when it obtains the target energy.

In the same way, a physical shutter is installed or an electrical circuit shutter is set just behind the sample, thus exciting light is prevented from irradiation to the light quantity detector like photomultiplier tube. By doing this, noise resulted from exciting light can be reduced and afterglow of the light source emitted after irradiation of exciting light and afterglow or scattered light from the lens, filter, mirror, or sample holder can be removed.

As a time-resolved fluorescence detection method using such a chopper, the art disclosed in Japanese Laid-open Patent Publication No. Hei 10-267844 is known. The art uses a first chopper so as to convert light to be entered to a sample to pulse light using the light source of exciting light as a continuous light source and uses a second chopper so as to detect only the target fluorescence or phosphorescence among light transmitted from the sample. By this method, afterglow of the light source and afterglow or scattered light from the lens, filter, mirror, or sample holder can be removed efficiently.

SUMMARY OF THE INVENTION

The art disclosed in Japanese Laid-open Patent Publication No. Hei 10-267844 (1998) must install two choppers independently and synchronize and control them by a PLL circuit, so that the device is inevitably complicated and increased in cost.

The present invention is intended to provide a fluorescence and phosphorescence measuring device that choppers are inserted in a plurality of parts of the optical path from the light source to the detection unit, and fluorescence or phosphorescence emitted only from a sample can be measured effectively, and the number of choppers according to this is reduced to one, thus few troubles are caused due to a simple structure, and the price is low, and measurement is available in high sensitivity and at a high SN ratio.

In a fluorescence measuring device or phosphorescence measuring device of the present invention, at the time of analysis and measurement of a sample, the optical path of exciting light emitted from the light source to the sample and the optical path of fluorescence or phosphorescence emitted from the sample to the light quantity detection unit are respectively shut off by using one light shielding plate.

When the optical paths are shut off on both sides of exciting light and detection, the source of exciting light does not need always to execute flashing (repetitively turning on and off) or generate a pulse and can be kept on continuously. By doing this, increasing and decreasing of the light quantity irradiated to a sample can be controlled by a circular chopper by the size of the gap through which light passes and the rotational speed of the disk.

DETAILED DESCRIPTION OF THE PREFERRED EMBODIMENTS

The progress of a laser device and the improvement of the video processing art such as a CCD camera, a photodiode array, and a photoelectric multiplier are remarkable. Further, the ultra-microanalytical art of substances resulted from organisms such as a gene and protein using a microchip or a microdevice is going to be largely progressed.

When sample analytical measurement is to be executed by a microdevice, a sample in a tubular or hollow container is irradiated by exciting light by a laser, and emitted phosphorescence or fluorescence is subjected to light measurement by a light measuring device or caught as an image of a CCD camera, and after data processing, the measured value is displayed or the sample is analyzed by using it.

The lens or filter is known to emit fluorescence or phosphorescence due to irradiation of light. Exciting light preferably does not reach the lens or filter of the detection unit. When reflection (changing of the optical path), focusing, or scattering of light is necessary, a mirror is used. It is said that the aluminum metallic material of a reflecting mirror does not emit fluorescence and phosphorescence.

The embodiments of a fluorescence or phosphorescence measuring device of the present invention will be explained in detail hereunder with reference to FIGS. 1 to 7.

[Embodiment 1]

Figure 1:
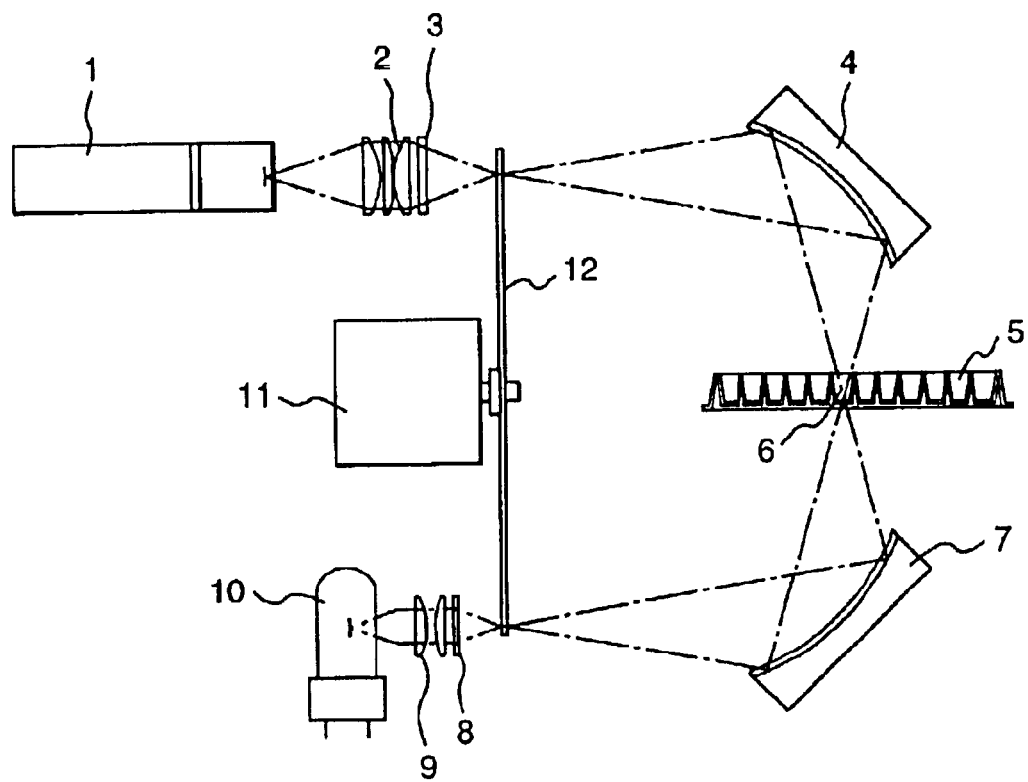
FIG. 1 is a schematic view of the optical system of a fluorescence and phosphorescence measuring device according to the present invention.

FIG. 1 shows a system layout diagram of the embodiment of the present invention. Light from a light source 1 such as a pulse generation light source like xenon flash lamp is focused by a lens system 2, passes through a selection filter 3 taking out only the wavelength component for excitation, then is focused by a focusing mirror 4 like dichroic mirror, and irradiated to a sample 6 distributed into a sample container 5 such as a microplate. Fluorescence or phosphorescence from the sample 6 is focused by a focusing mirror 7 on the opposite side, and short-wavelength light which is exciting light is removed, and the fluorescence or phosphorescence passes through a selection wave length filter 8 for taking out light having a necessary wavelength band and passes through a lens system 9, and the light quantity is converted through the detector like photomultiplier tube and its electric circuit.

A motor 11 and a chopper blade 12 will be explained later. Here, when as a sample, europium and ligand, and its complex or labeled protein is used, the exciting wavelength is set to about 340 nm and the wavelength of fluorescence of phosphorescence to be detected is set to about 615 nm.

It is said that the aluminum metallic material of the reflecting mirror does not emit fluorescence and phosphorescence.

Figure 2:
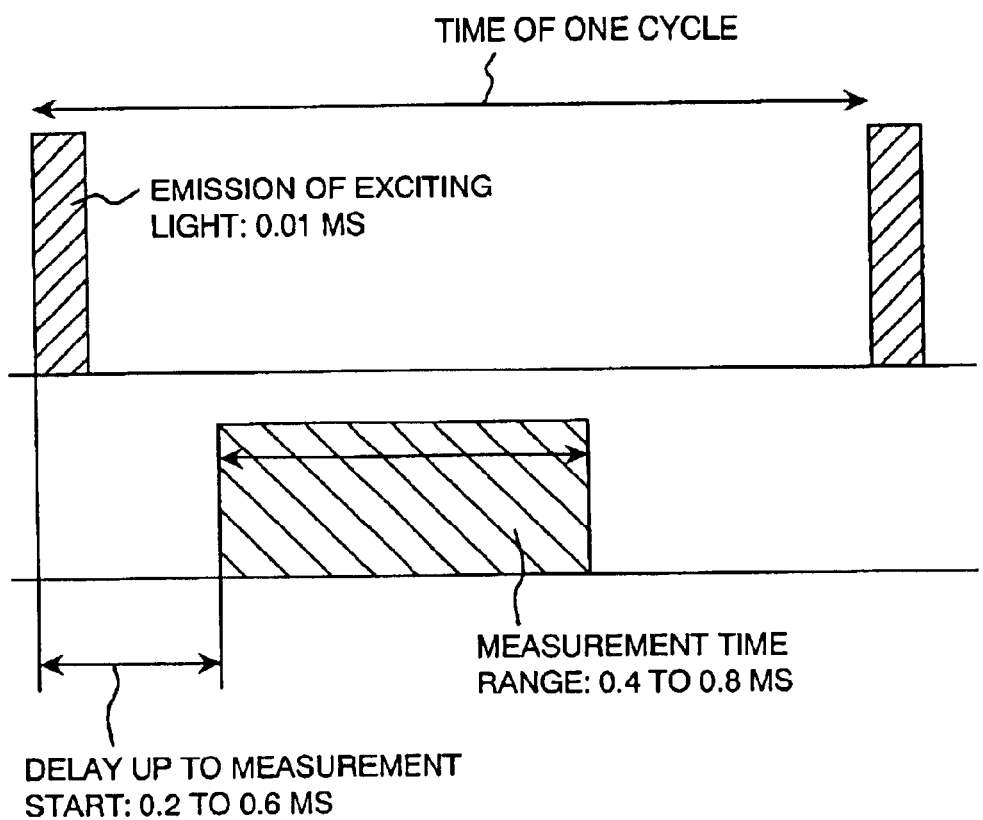
FIG. 2 is a timing chart example of a device when the present invention is not used.

FIG. 2. shows an example of the timing chart of this time-resolved fluorescence measurement. The excitation light of pulse emission from the light source is only for a very short period such as about 0.01 ms. Fluorescence or phosphorescence from a sample excited by this light is set so as to open the gate of the light detector at a point of time 0.2 to 0.6 ms delayed after starting of emission of excitation light from the light source, thereafter measure for about 0.4 to 0.8 ms, close the gate of the signal detector, and move to the next exciting light emission timing.

In this case, when fluorescence and phosphorescence are to be measured in high sensitivity, the fluorescence and phosphorescence components emitted from the lens system or filter and afterglow after end of pulse excitation of the light source cannot be ignored and are detected as measured noise.

Figure 3:
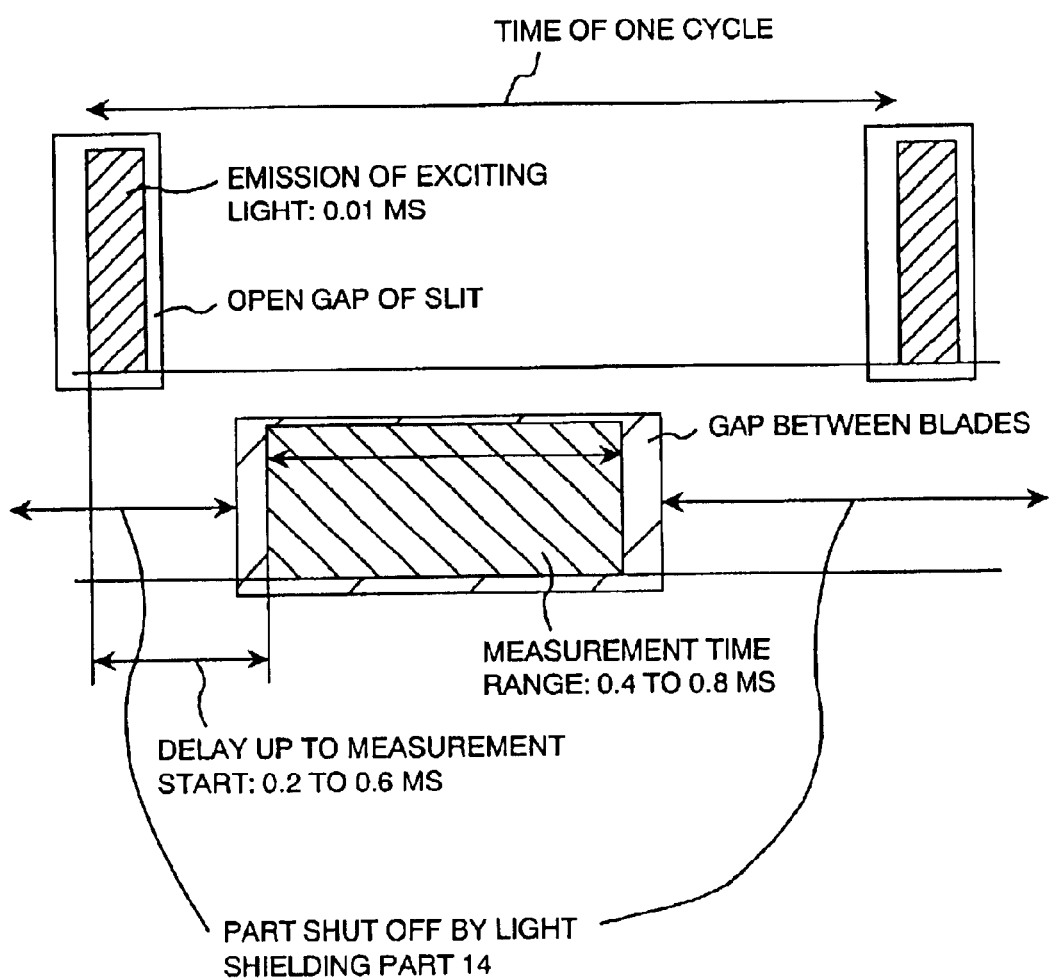
FIG. 3 is a timing chart example according to the present invention.

FIG. 3 shows a schematic view in the measurement timing of this system. By exciting light from the light source, fluorescence and phosphorescence intrinsic to the material are always emitted from a lens system 2, 9 and a filter 3, 8. Further, light is excited from the afterglow from the light source and fluorescence and phosphorescence from the light are overlaid with them.

Therefore, according to the embodiment of the present invention, to solve the aforementioned problem, in the system layout shown in FIG. 1, the motor 11 and the chopper 12 connected to the motor shaft are installed.

Figure 4:
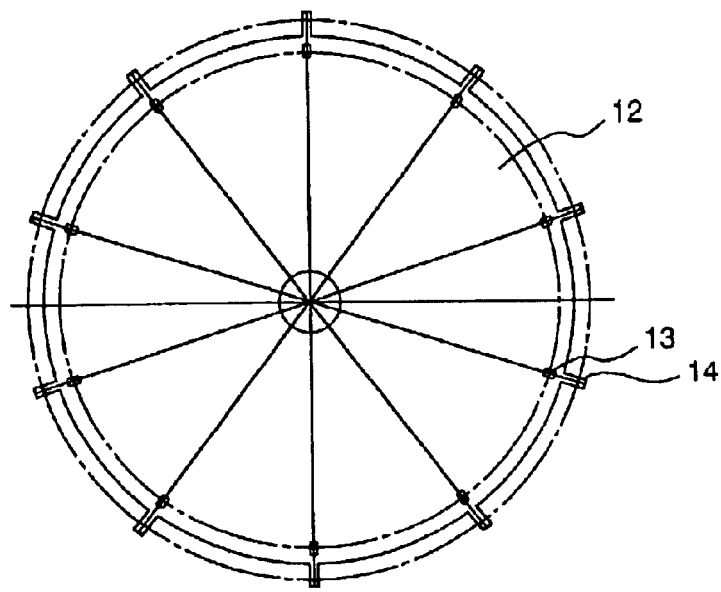
FIG. 4 is a schematic view of a chopper according to the present invention.

The chopper is structured as shown in FIG. 4. A plurality of pairs of a slit 13 for passing light through the optical path between the light source and a sample to be measured and a light shielding part 14 for shielding light on the optical path between the sample to be measured and the detector are installed on the light shielding plate and each pair of a slit 13 and a light shielding part 14 are installed almost in the radial direction of the circular light shielding plate and positioned in different places in the radial direction.

The position relationship between the slits and the light shielding parts in the radial direction can be set freely according to the arrangement way of the optical system. Further, "almost in the radial direction" is referred to as "almost on the same radius" and "almost" means "no need to be strictly in the same radial position".

When the timing that the slit 13 for passing light on the optical path between the light source and the sample to be measured passes light and the timing that the light shielding part 14 for shielding light on the optical path between the sample to be measured and the detector shields light coincide with each other even slightly, the effect of this embodiment can be realized.

Figure 8A:
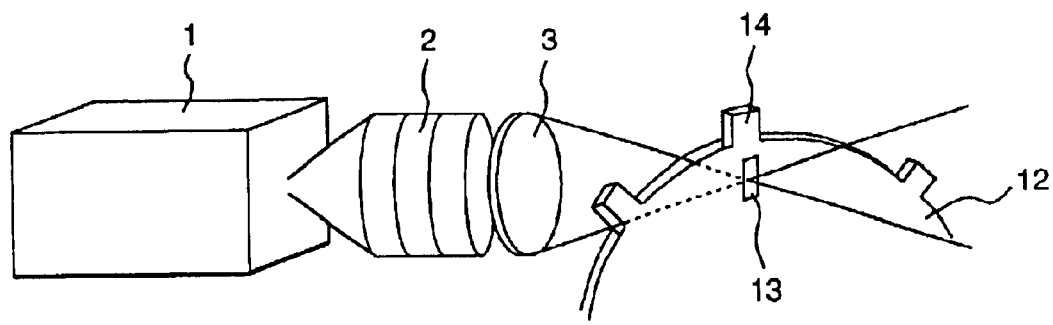
FIGS. 8a and 8b are detailed drawings showing the relation between the slits and light shielding part and the optical path of the present invention.
Figure 8B:
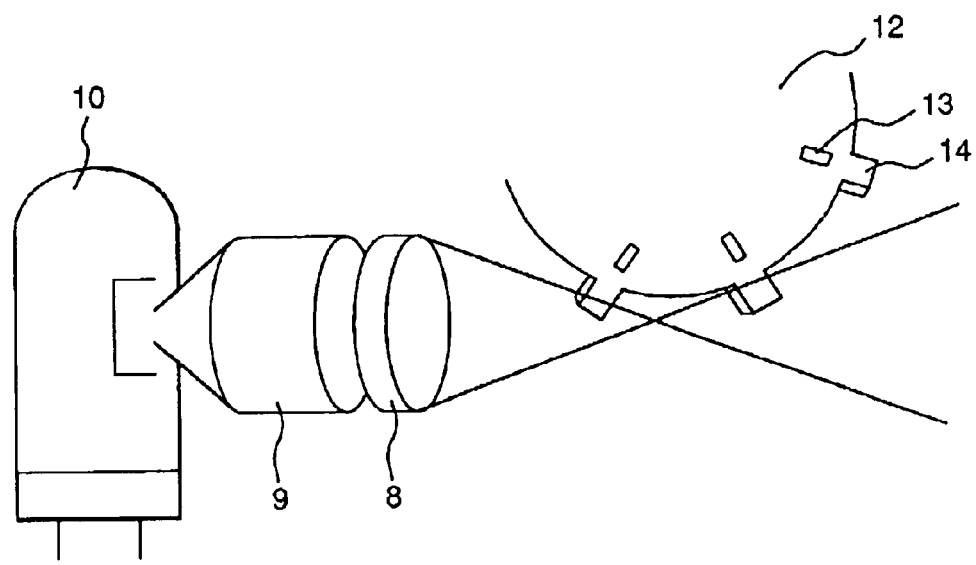

In the drawing, the inside slits 13 are inserted into the focusing path on the light source side and the outside light shielding parts 14 are inserted into the optical path between the detectors from the sample as shown in the drawing (refer to FIGS. 8a and 8b). FIG. 3 shows a schematic view at the measurement timing. By timing pulse generation of the light source, a timing chart as shown in FIG. 3 can be drawn.

The chopper, during irradiation to the sample 6 from the light source 1, shuts off the optical path to the light detector 10 from the sample 6 and does not lead light to the light detector 10. Further, the chopper may be structured so as to prevent light of the light source 1 from irradiation to the sample 6 during leading of light from the sample 6 to the detector 10.

Further, when the chopper is rotated at high speed, the repetitive measuring time can be shortened. Further, the opening time of the slits for exciting light can be shortened sufficiently and even if the light source uses continuous light, pulse excitation can be realized. Further, when a pulse light source such as a flash lamp is to be used as a light source, if the slits trigger the pulse light source in the timing that exciting light passes through the optical path, the pulse light source can execute in the same way. In this case, passing through the slits must be monitored and a photocoupler not shown in the drawing may be used.

[Embodiment 2]

Figure 5:
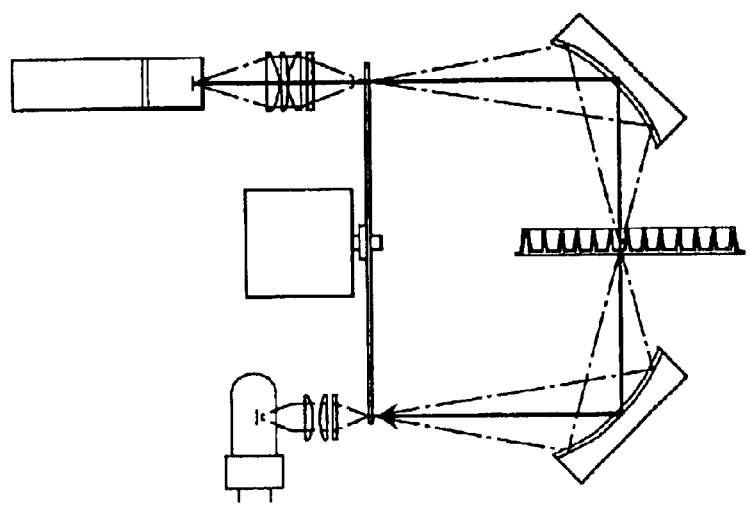
FIG. 5 is a drawing showing an optical path of exciting light generated from a light source according to the present invention.

FIG. 5 shows, when the optical path from the light source of exciting light to a sample is opened, the optical path of light emitted from the light source when the fluorescence or phosphorescence optical path from the sample to the detection unit is shut off. It is found that the light does not reach the lens and filter of the detection unit and unnecessary scattered light and fluorescence or phosphorescence are not generated in those parts.

Figure 6:
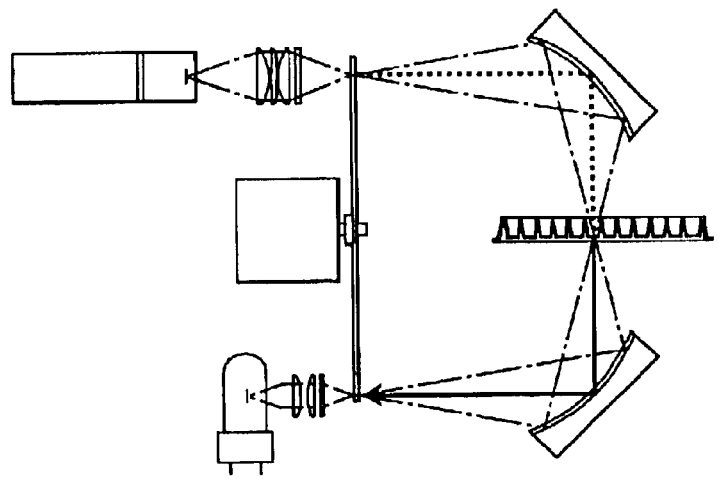
FIG. 6 is a drawing showing an optical path of fluorescence or phosphorescence generated from a light source according to the present invention.

FIG. 6 shows, when the optical path from the light source of exciting light to the sample is shut off, the optical path of light generated from the sample when the fluorescence or phosphorescence optical path from the sample to the detection unit is opened. It is found that fluorescence or phosphorescence from the sample is caught by the light detector and exciting light or scattered light from the light source does not reach the detection unit.

Figure 7:
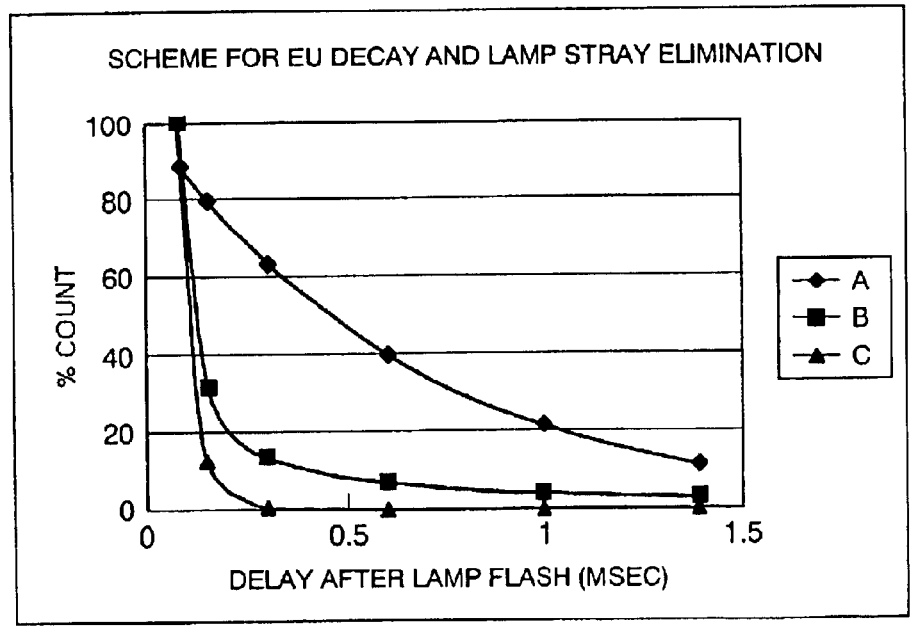
FIG. 7 is a drawing showing an example of a change with time of europium phosphorescence generated from a sample according to the present invention and a change with time of background noise at the time of measurement.

The background reduction effect of the present invention is shown in a schematic view in FIG. 7. Symbol A indicates that when a sample labeled with europium and its ligand via a complex suited to europium is used as protein, a sample excited by a xenon flash lamp emits phosphorescence. Phosphorescence decays with time, though the half-life of phosphorescence is comparatively long. Symbol B indicates decay of background noise when the present invention is not used and no chopper is used.

The light quantity measured after flashing of the . . . flash lamp decays suddenly, though by stray light such as light emitted from the lens and filter other than the sample due to irradiation of afterglow or exciting light after turning the light source off, background noise is detected though it is low. Symbol C indicates decay of background noise when the present invention is used.

Unnecessary light is not irradiated to the lens and filter of the light detector, and afterglow, scattered light, and stray light from the lens and filter on the exciting light side are not caught by the light detector, and fluorescence or phosphorescence resulted from them is not detected.

With respect to the light quantity measured for 0.4 ms to 0.8 ms, the value of (light quantity obtained by A)/(light quantity obtained by C) is larger than the value of (light quantity obtained by A)/(light quantity obtained by B) and it is found that the SN ratio is greatly improved.

(1) According to the present invention, noise of a fluorescence measuring device and a phosphorescence measuring device is reduced, and the background resulted from the device or sample container is lowered, and as a result, the SN ratio at the time of measurement is increased, and the lower detection limit or measuring sensitivity can be improved.

(2) According to the present invention, by one chopper of the fluorescence measuring device and phosphorescence measuring device, both optical paths from the light source to a sample and from the sample to the light detector can be shut off. As a result, a device of low cost and high reliability can be provided.

(3) According to the present invention, by the time decomposition fluorescence measuring method or the fluorescence or phosphorescence measuring method, the exciting light source enables measurement by continuous light free of pulse flickering of a lamp or a laser.

(4) According to the present invention, a lens or a filter is not used in the optical path between the light shielding mechanisms of the fluorescence measuring device and phosphorescence measuring device and fluorescence or phosphorescence resulted from it can be eliminated. As a result, the background resulted from the device or sample container is lowered, and noise is reduced, and moreover the lower detection limit or measuring sensitivity of the device can be improved.

What is claimed is:

1. A fluorescence and phosphorescence measuring device comprising:

a light source;

an optical system for selecting, taking out, and directing light with a wavelength necessary for measurement from light emitted from said light source;

a detector of fluorescence or phosphorescence generated from a sample irradiated by said measurement light (selected, taken out, and directed by said optical system);

an optical path shielding mechanism arranged to temporarily block a first optical path between said light source and said sample, and to temporarily block a second optical path between said sample and said detector; and a first concave mirror installed in said first optical path between said optical path shielding mechanism and said sample, and a second concave mirror installed in said second optical path between said sample and said optical path shielding mechanism, no lens or filter emitting fluorescence or phosphorescence by irradiation of exciting light from said light source being installed in said first optical path between said optical path shielding mechanism and said sample or in said second optical path between said sample and said optical path shielding mechanism.

2. A fluorescence and phosphorescence measuring device according to claim 1, wherein said light source is a light source continuously kept on, and said optical path shielding mechanism between said sample to be measured and said detector operates so as to shield said second optical path in a time zone that said light from said light source enters said sample to be measured, and said optical path shielding mechanism between said light source and said sample to be measured operates so as to shut off said first optical path in a time zone that said fluorescence or phosphorescence emitted from said sample to be measured enters said detector.

3. A fluorescence and phosphorescence measuring device according to claim 1, wherein said light source is a light source for generating a pulse.

4. A fluorescence and phosphorescence measuring device according to claim 1, wherein said optical path shielding mechanism includes a generally circular light shielding plate and installs a slit part for passing light through said first optical path between said light source and said sample to be measured, and a light shielding part for shielding light on said second optical path between said sample to be measured and said detector, said slit part and light shielding part being paired on said light shielding plate.

5. A fluorescence and phosphorescence measuring device according to claim 4, wherein said pair of slit part and light shielding part are installed almost in a radial direction of said light shielding plate and positioned in different places in said radial direction.

6. A fluorescence and phosphorescence measuring device according to claim 1, wherein at a time of measurement of fluorescence or phosphorescence, both of said first and second optical paths are blocked by said optical path shielding mechanism, and wherein said optical path shielding mechanism is a single light shielding plate.

7. A fluorescence and phosphorescence measuring device according to claim 1, wherein said optical path shielding mechanism is a single light shielding plate.

8. A fluorescence and phosphorescence measuring device according to claim 1, wherein said first and second concave mirrors are opposed to each other.

9. A fluorescence and phosphorescence measuring device according to claim 8, wherein said optical path shielding mechanism is a single light shielding plate.

10. A fluorescence and phosphorescence measuring device comprising:

a light source;

an optical system for selecting, taking out, and directing light with a wavelength necessary for measurement from light emitted from said light source;

a detector of fluorescence or phosphorescence generated from a sample irradiated by said measurement light (selected, taken out, and directed by said optical system);

an optical path shielding mechanism arranged to temporarily block a first optical path between said light source and said sample, and to temporarily block a second optical path between said sample and said detector; and a mirror installed in said first optical path between said optical path shielding mechanism and said sample, no lens or filter emitting fluorescence or phosphorescence by irradiation of exciting light from said light source being installed in said first optical path between said optical path shielding mechanism and said sample or in said second optical path between said sample and said optical path shielding mechanism.

11. A fluorescence and phosphorescence measuring device according to claim 10, wherein said mirror is a concave mirror.

* * * * *